US012727778B2

(12) United States Patent
Alcala

(10) Patent No.: US 12,727,778 B2
(45) Date of Patent: Sep. 8, 2026

(54) DEVICES, SYSTEMS, AND METHODS FOR ASSESSING LUNG CHARACTERISTICS VIA REGIONAL IMPEDANCE AND PATIENT POSITIONING

(71) Applicant: Timpel Medical B.V., Eindhoven (NL)

(72) Inventor: Glasiele Cristina Alcala, Sao Paulo (BR)

(73) Assignee: Timpel Medical B.V., Eindhoven (NL)

( * ) Notice: Subject to any disclaimer, the term of this patent is extended or adjusted under 35 U.S.C. 154(b) by 884 days.

(21) Appl. No.: 17/767,336

(22) PCT Filed: Oct. 6, 2020

(86) PCT No.: PCT/IB2020/059384
§ 371 (c)(1),
(2) Date: Apr. 7, 2022

(87) PCT Pub. No.: WO2021/070059
PCT Pub. Date: Apr. 15, 2021

(65) Prior Publication Data

US 2022/0378314 A1 Dec. 1, 2022

Related U.S. Application Data

(60) Provisional application No. 62/911,887, filed on Oct. 7, 2019.

(51) Int. Cl.
*A61M 16/00* (2006.01)
*A61B 5/00* (2006.01)
(Continued)

(52) U.S. Cl.
CPC .......... *A61B 5/0536* (2013.01); *A61B 5/1128* (2013.01); *A61B 5/113* (2013.01); *A61B 5/70* (2013.01); *A61B 5/7264* (2013.01)

(58) Field of Classification Search
CPC . A61B 5/0536; A61B 5/113; A61B 5/70–704; A61B 5/08;
(Continued)

(56) References Cited

U.S. PATENT DOCUMENTS

| | | | |
|---|---|---|---|
| 2007/0062528 | A1 | 3/2007 | Heinonen et al. |
| 2008/0185009 | A1 | 8/2008 | Choncholas et al. |

(Continued)

FOREIGN PATENT DOCUMENTS

| | | | |
|---|---|---|---|
| AU | 2012243429 | A1 | 11/2013 |
| CN | 103002802 | A | 3/2013 |

(Continued)

OTHER PUBLICATIONS

Ukere, A et al. "Perioperative Assessment of Regional Ventilation during Changing Body Positions and Ventilation Conditions by Electrical Impedance Tomography." British journal of anaesthesia: BJA 117.2 (2016 (Year: 2016).*

(Continued)

*Primary Examiner* — Matthew Kremer
*Assistant Examiner* — Aaron Merriam
(74) *Attorney, Agent, or Firm* — TraskBritt

(57) ABSTRACT

Methods and systems for assessing characteristics of a lung of a patient. A method includes, during an applied positive end expiratory pressure, identifying a first position of a patient, acquiring first impedance data representative of at least a region of patient's lung when the patient is in the first position, during the applied positive end expiratory pressure, identifying a second different position of a patient, acquiring second impedance data representative of at least the region of patient's lung when the patient is in the second position, comparing the first impedance data with the second impedance data, and determining whether the applied positive end expiratory pressure is sufficient to effectuate recruitment.

19 Claims, 8 Drawing Sheets

(51) Int. Cl.

| | |
|---|---|
| ***A61B 5/0536*** | (2021.01) |
| ***A61B 5/08*** | (2006.01) |
| ***A61B 5/091*** | (2006.01) |
| ***A61B 5/11*** | (2006.01) |
| ***A61B 5/113*** | (2006.01) |
| ***A61M 16/20*** | (2006.01) |
| ***G16H 20/40*** | (2018.01) |

(58) Field of Classification Search

CPC ... A61M 2205/3334–3344; A61M 2210/1039; A61M 16/204–205; A61M 2230/46; A61M 2230/62; A61M 2230/65

See application file for complete search history.

(56) References Cited

U.S. PATENT DOCUMENTS

| | | | | |
|---|---|---|---|---|
| 2008/0202527 A1* | 8/2008 | Hutchinson | A61M 16/024 128/204.23 |
| 2013/0190577 A1* | 7/2013 | Brunner | A61B 5/6802 600/301 |
| 2019/0038173 A1* | 2/2019 | Gärber | A61B 5/7264 |
| 2019/0246949 A1 | 8/2019 | Holzhacker | |

FOREIGN PATENT DOCUMENTS

| | | | |
|---|---|---|---|
| CN | 114585303 | A | 6/2022 |
| JP | 2010-516345 | A | 5/2010 |
| JP | 2021-513443 | A | 5/2021 |
| WO | 2012/045188 | A1 | 4/2012 |
| WO | 2012/139159 | A1 | 10/2012 |
| WO | 2015/048917 | A1 | 4/2015 |

OTHER PUBLICATIONS

Spadaro, Savino et al. "Variation of Poorly Ventilated Lung Units (Silent Spaces) Measured by Electrical Impedance Tomography to Dynamically Assess Recruitment." Critical care (London, England) 22.1 (2018) (Year: 2018).*

European Communication pursuant to Article 94(3) EPC for European Application No. 20792743.5, dated Jun. 6, 2023, 7 pages.

Frerichs et al., "Granvity-dependent phenomena in lung ventilation determined by functional EIT", Physiological Measurement, Institute of Physics Publishing, Bristol, GB, vol. 17, No. 4A, Nov. 1, 1996, 9 pages.

International Search Report for International Application No. PCT/IB2020/059384, mailed Jan. 18, 2021, 6 pages.

International Written Opinion for International Application No. PCT/IB2020/059384, mailed Jan. 18, 2021, 8 pages.

Japanese Notice of Reasons for Refusal for Japanese Application No. 2022-521023, mailed Mar. 27, 2023, 6 pages with English translation.

First Office Action and Search Report of Chinese Patent Application No. 202080070081.6, issued Jun. 19, 2025, 21 pages with English translation.

European Communication pursuant to Article 94(3) EPC for European Application No. 20792743.5, dated Apr. 10, 2025, 4 pages.

Second Office Action and Search Report of Chinese Patent Application No. 202080070081.6, issued Jan. 14, 2026, 27 pages with English translation.

Eronia, Nilde et al. "Bedside selection of positive end-expiratory pressure by electrical impedance tomography in hypoxemic patients: a feasibility study." Annals of intensive care vol. 7,1 (2017): 76. 10 pages. doi:10.1186/s13613-017-0299-9.

Third Office Action and Search Report of Chinese Patent Application No. 202080070081.6, issued May 14, 2026, 31 pages with English translation.

* cited by examiner 400
410
418
426
416
402
412
405
POSITION SENSOR
404
EIT SYSTEM
414
422
428
430
420
424
432
406
408

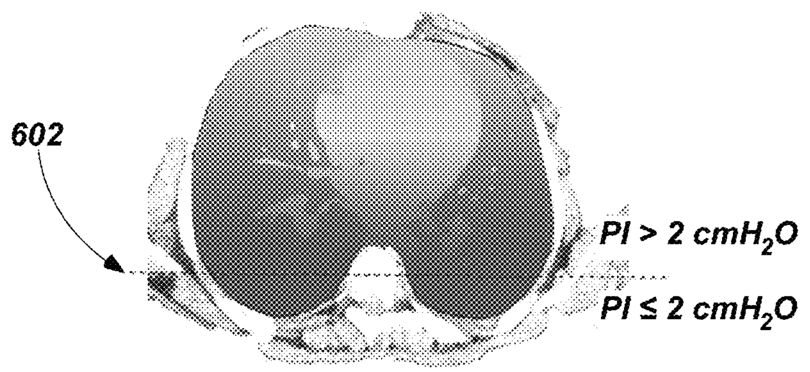

*Spinal cord line is perpendicular to the gravity vector*

The alveolar expansion is dependent on transpulmonary pressure; since dependent lung regions have transpulmonary pressure ( PI) ≤ 2 $cmH_2O$ vs PI > 2 $cmH_2O$ in non dependent lung regions, posterior region present more collapse than anterior regions

*FIG. 6A*

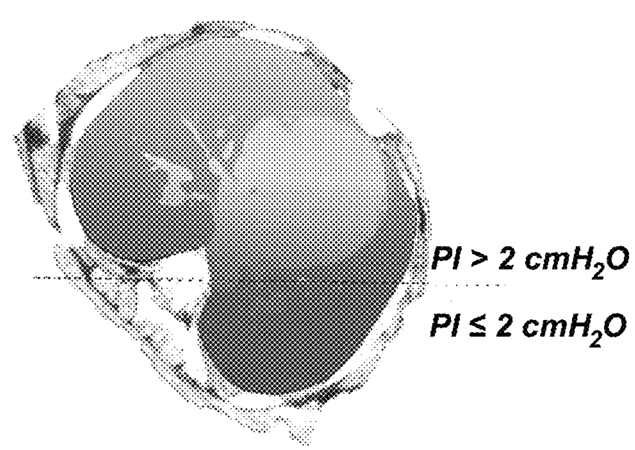

*Spinal cord line is perpendicular to the gravity vector*

The same phenomenon occurs when the lung is in the lateral decubitus position, however, if the ideal PEEP is used (above critical closing pressure), the regions recruited when put in the superior position will be kept open when they are came back to supine position

*FIG. 6B*

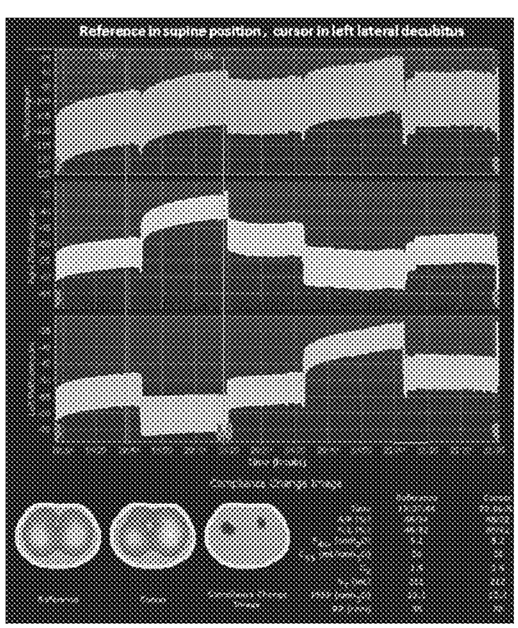

1. Left lateral decubitus as compared to supine implied in higher aeration and lower Vt of the right side of the lung. Improved regional compliance at the left, impaired compliance at the right.

*FIG. 7A*

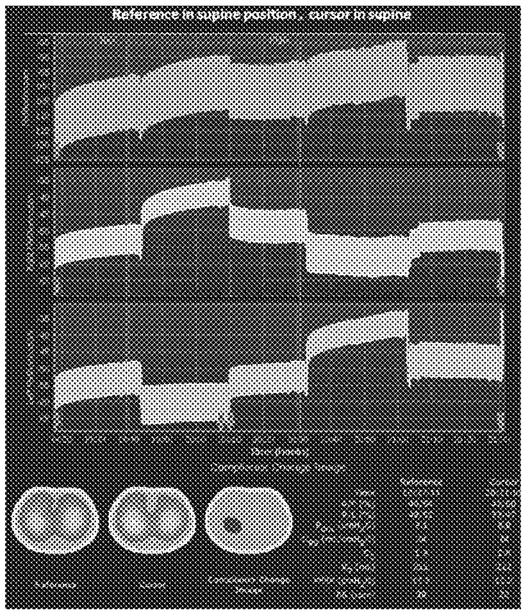

2. After returning to supine position, right and global aeration were higher and compliance at the left lung improved, meaning that the PEEP level (kept at a similar level) was enough to sustain the recruitment that occurred during left lateral positioning (step 1)

*FIG. 7B*

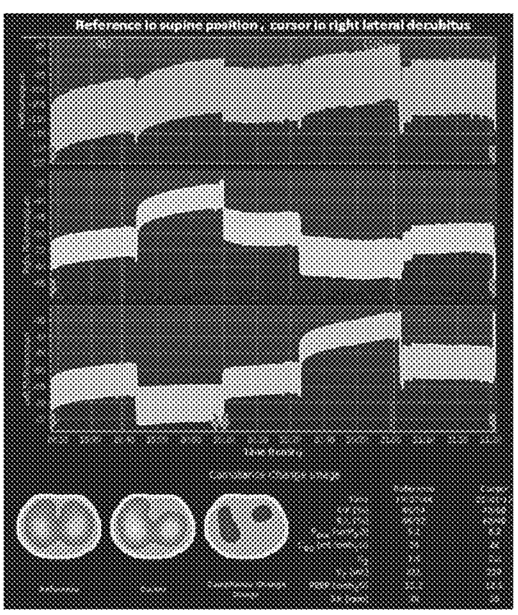

2. Right lateral decubitus as compared to supine implied in higher aeration and lower Vt of the left side of the lung. Improved regional compliance at the right, impaired compliance at the left.

*FIG. 7C*

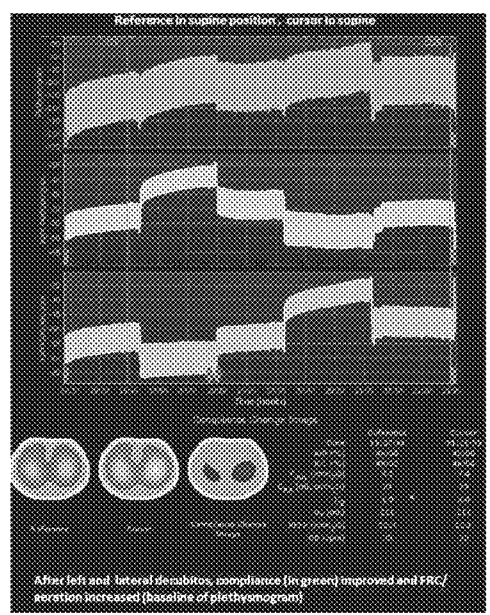

2. After returning to supine position, right, left and global aeration were higher and compliance at the right and left sides improved. The PEEP level (kept at a similar level) was enough to sustain the recruitment that occurred during left and right lateral positioning.

*FIG. 7D*

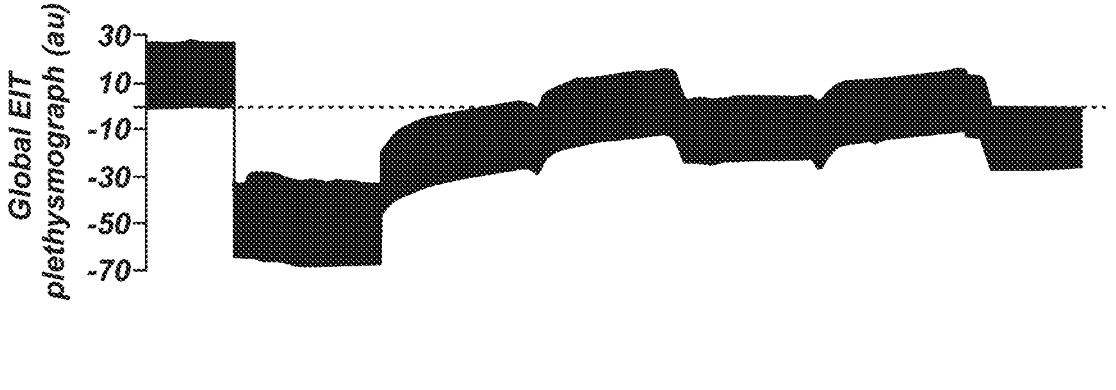
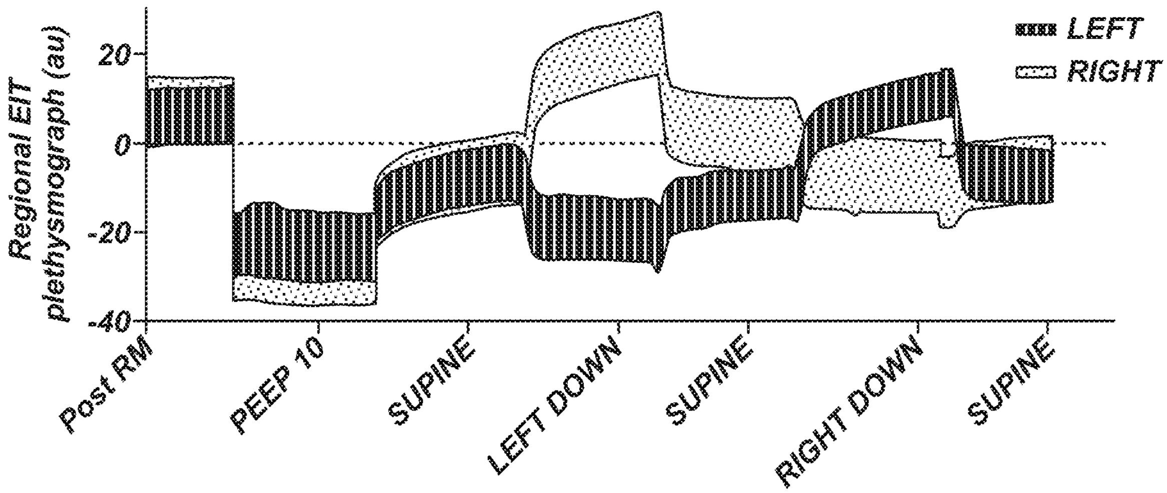
*FIG. 8*

DEVICES, SYSTEMS, AND METHODS FOR ASSESSING LUNG CHARACTERISTICS VIA REGIONAL IMPEDANCE AND PATIENT POSITIONING

CROSS-REFERENCE TO RELATED APPLICATIONS

This application is a national phase entry under 35 U.S.C. § 371 of International Patent Application PCT/IB2020/059384, filed Oct. 6, 2020, designating the United States of America and published as International Patent Publication WO 2021/070059 A1 on Apr. 15, 2021, which claims the benefit under Article 8 of the Patent Cooperation Treaty to U.S. Patent Application Ser. No. 62/911,887, filed Oct. 7, 2019.

TECHNICAL FIELD

The disclosure relates to electrical impedance tomography systems generally, and more specifically, to devices, systems, and methods to determine effective PEEP levels for recruiting alveoli of a patient, a patient's potential responsiveness to an alveolar recruitment maneuver using electrical impedance tomography, and characteristics of the patients lungs.

BACKGROUND

The treatment of acute respiratory distress syndrome (ARDS) includes a proper mechanical ventilation strategy. The alveolar recruitment maneuver (ARM) is an intervention applied in moderate and severe cases of ARDS. ARM is a transitory and controlled increase in mechanical ventilator pressure delivered to the lungs aiming to open previously collapsed alveoli. However, some patients respond well to an ARM maneuver (referred to herein as "responders"), while other patients do not respond well to the ARM maneuver (referred to herein as "non-responders"). Caregivers should assess a patient's responsiveness to an ARM maneuver, and apply it only on the patients that will benefit from the ARM maneuver (responders). The ARM maneuver may also introduce some additional risks, such as Ventilatory Induced Lung Injury (VILI) and hemodynamic impairment. Conventional methods for determining whether the patient is responsive to an ARM maneuver include Computed Tomography (CT) and Pulmonary Mechanics.

CT may be used as a method to estimate amount of lung collapse (e.g., in grams and/or in percentage of lung weight), and the amount of lung that was reopened responsive to an ARM. However, it provides only static images, it requires the use of excessive radiation (it is necessary to scan the whole lung at two different positive and expiratory pressure (PEEP) levels—at least), and it requires long ins/expiratory pauses (with risks of hypercapnia and hemodynamic impairment). Finally it is necessary to transport the patient from the ICU to the radiology department, with well known risks.

Pulmonary Mechanics may be used as a method to determine a patient's responsiveness using PEEP therapy with a mechanical ventilator. The patient is provided PEEP therapy at a first PEEP. A first end expiratory lung volume (EELV) is measured from the patient. PEEP therapy is provided to the patient at a second PEEP. A second EELV is measured from the patient. A difference from the first EELV and the second EELV may be calculated. A value indicative of the patient's response to PEEP therapy is calculated from the difference between the first EELV and the second EELV. AEELV/functional residual capacity (FRC) ratio may be used to differentiate high recruiters from low recruiters. However, these procedures are limited to patients under ventilatory support and require a PEEP increase (maneuver can be incremental or decremental), with known risk of hemodynamic impairment. Other assessments that use regional information of impedance change and EIT, such as the responsiveness to a recruitment maneuver, also require a change in PEEP.

BRIEF DESCRIPTION OF THE DRAWINGS

FIG. 6A is a schematic representation of a cross-section of a patient's torso in a supine position;

FIG. 6B is a schematic representation of a cross-section of a patient's torso in a lateral position;

FIGS. 7A-7D shows graphs that depict information from a patient in various positions;

FIG. 8 shows a graph depicting a global EIT plethysmograph and a regional EIT plethysmograph while orienting the patient in various positions.

DETAILED DESCRIPTION

Figure 1:
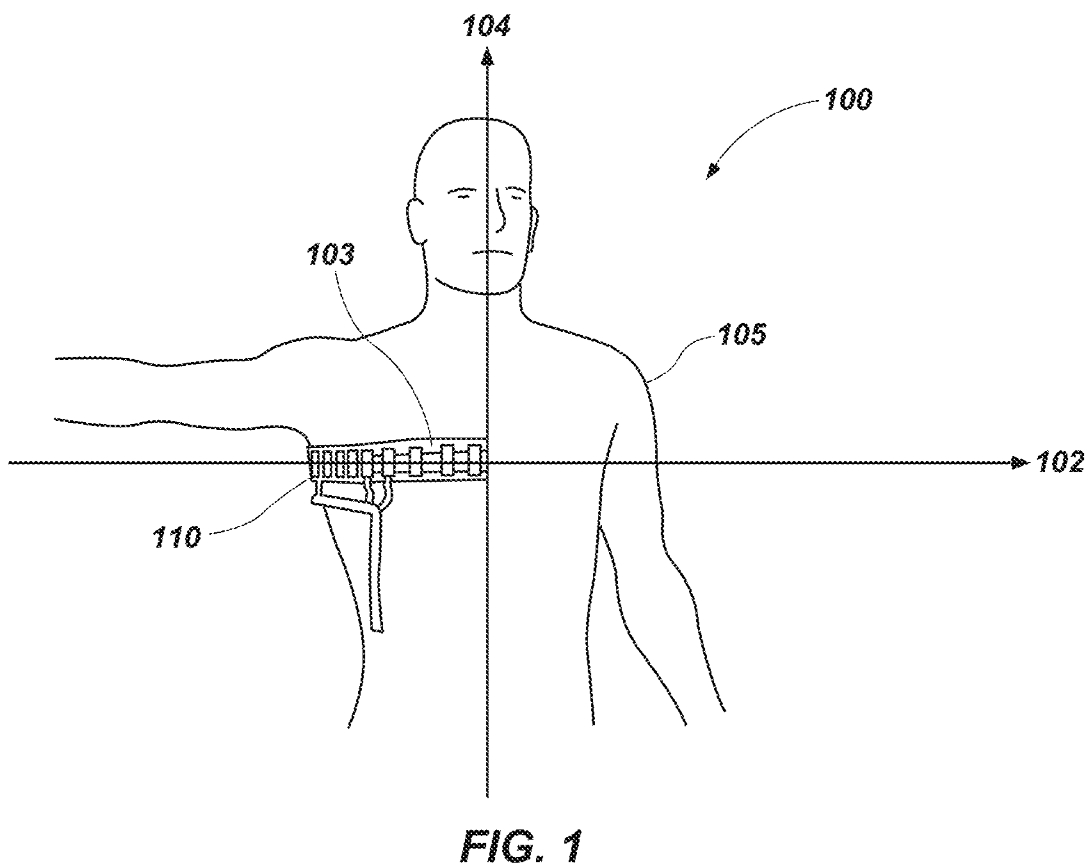
FIG. 1 is a schematic diagram of a portion of an EIT system showing a plurality of electrodes positioned around a region of interest of a patient according to one or more embodiments of the present disclosure.

This provisional patent application is related to Appendix A attached hereto, which also forms a part of the present disclosure. The published documents referenced in the References section at the end of Appendix A are hereby incorporated herein by this reference.

In the following detailed description, reference is made to the accompanying drawings, which form a part hereof, and in which is shown by way of illustration specific embodiments in which the disclosure may be practiced. These embodiments are described in sufficient detail to enable those of ordinary skill in the art to practice the disclosure. It should be understood, however, that the detailed description and the specific examples, while indicating examples of embodiments of the disclosure, are given by way of illustration only and not by way of limitation. From this disclosure, various substitutions, modifications, additions rearrangements, or combinations thereof within the scope of the disclosure may be made and will become apparent to those of ordinary skill in the art.

In accordance with common practice, the various features illustrated in the drawings may not be drawn to scale. The illustrations presented herein are not meant to be actual views of any particular apparatus (e.g., device, system, etc.) or method, but are merely representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus or all operations of a particular method.

Information and signals described herein may be represented using any of a variety of different technologies and techniques. For example, data, instructions, commands, information, signals, bits, symbols, and chips that may be referenced throughout the description may be represented by voltages, currents, electromagnetic waves, magnetic fields or particles, optical fields or particles, or any combination thereof. Some drawings may illustrate signals as a single signal for clarity of presentation and description. It should be understood by a person of ordinary skill in the art that the signal may represent a bus of signals, wherein the bus may have a variety of bit widths and the disclosure may be implemented on any number of data signals including a single data signal.

The various illustrative logical blocks, modules, and circuits described in connection with the embodiments disclosed herein may be implemented or performed with a general purpose processor, a special purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A general-purpose processor may be considered a special-purpose processor while the general-purpose processor executes instructions (e.g., software code) stored on a computer-readable medium. A processor may also be implemented as a combination of computing devices, e.g., a combination of a DSP and a microprocessor, a plurality of microprocessors, one or more microprocessors in conjunction with a DSP core, or any other such configuration.

Also, it is noted that embodiments may be described in terms of a process that may be depicted as a flowchart, a flow diagram, a structure diagram, or a block diagram. Although a flowchart may describe operational acts as a sequential process, many of these acts can be performed in another sequence, in parallel, or substantially concurrently. In addition, the order of the acts may be re-arranged. A process may correspond to a method, a function, a procedure, a subroutine, a subprogram, etc. Furthermore, the methods disclosed herein may be implemented in hardware, software, or both. If implemented in software, the functions may be stored or transmitted as one or more instructions or code on computer-readable media. Computer-readable media include both computer storage media and communication media, including any medium that facilitates transfer of a computer program from one place to another.

As used herein, the singular forms following "a," "an," and "the" are intended to include the plural forms as well, unless the context clearly indicates otherwise.

As used herein, the term "may" with respect to a material, structure, feature, or method act indicates that such is contemplated for use in implementation of an embodiment of the disclosure, and such term is used in preference to the more restrictive term "is" so as to avoid any implication that other compatible materials, structures, features, and methods usable in combination therewith should or must be excluded.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

As used herein, the term "substantially" in reference to a given parameter, property, or condition means and includes to a degree that one skilled in the art would understand that the given parameter, property, or condition is met with a small degree of variance, such as within acceptable manufacturing tolerances. For example, a parameter that is substantially met may be at least about 90% met, at least about 95% met, or even at least about 99% met.

As used herein, the term "about" used in reference to a given parameter is inclusive of the stated value and has the meaning dictated by the context (e.g., it includes the degree of error associated with measurement of the given parameter, as well as variations resulting from manufacturing tolerances, etc.).

As used herein, the term "supine position" may refer to a position where a person (e.g., patient) is lying generally horizontally with the patient's face and torso facing upward.

As used herein, the term "lateral position" may refer to a position where a person is lying generally horizontally but with one side (e.g., right or left side) tilted downward with the other side tilted upward. For instance, the person may be tilted 30°, 45°, or 60° toward one side. For example, lateral position may refer to a position such as that depicted in FIG. 6B. In some embodiments, lateral position may refer to a position where a person is lying on one side (e.g., a right or left side).

As used herein, the term "prone position" may refer to a position where a person is lying generally horizontally with the patient's torso facing downward.

Embodiments of the present disclosure include an electrical impedance tomography (EIT) and position determination system for assessing lung characteristics (e.g., a change in compliance, a change in regional Tidal Volume (i.e., Tidal Impedance), a change in aeration (e.g., end expiratory lung volume, end expiratory lung impedance, baseline of plethysmograph, etc.)), etc., without significant changes in PEEP levels. Embodiments of the present disclosure include an EIT and position determination system for determining an effective PEEP level to apply to a patient to effectuate alveoli recruitment. In some embodiments, the effective PEEP level may be a minimal PEEP level that reduces a likelihood of damaging the lung and impairing hemodynamics while keeping alveoli open. Additionally, embodiments of the present disclosure include an EIT and position determination system for assessing an effect of a positioning recruitment maneuver for recruiting previously collapsed areas and/or sustaining the alveoli open and/or impairing of homogeneity of ventilation.

In some embodiments, the EIT and position determination system include an EIT device and one or more position sensors. EIT is an imaging technique involving the positioning of electrodes via an electrode belt placed around a region of a patient's body (e.g., around the patient's chest for imaging of a lung), injecting electrical excitation signals through a pair of electrodes, and measuring the induced response signals detected by the other electrodes of the electrode belt. As a result, the EIT system may generate an image based on the voltage measurements indicating estimated impedance values. In contrast with other imaging techniques, EIT is non-invasive and does not have certain exposure risks that might limit the number and frequency of monitoring actions (e.g., as with techniques such as X-rays). As a result, EIT is suitable for continuously monitoring the condition of the patient, with particular application to monitoring the patient's lungs as the measurements may be used to determine respiratory and hemodynamic parameters of the patient and monitor a real-time two-dimensional image.

Embodiments of the disclosure may be implemented by Electrical Impedance Tomography (EIT), or by a combination of information provided by EIT and flow and/or pressure sensors (e.g., pulmonary mechanics using gas monitoring sensors). Embodiments may also be implemented during tidal breaths, without requiring increases in PEEP. In some embodiments, information at the pixel level in EIT images (e.g., the location of the pixel, the pixel aeration changes, and the pixel compliance changes during a position changing maneuver) may be combined to produce more accurate and regional quantification.

FIG. 1 is a schematic diagram of a portion of an EIT system 100 showing a plurality of electrodes 110 positioned around a region of interest (e.g., thorax) 102 of a patient 105. The electrodes 110 of conventional EIT systems 100 are typically physically held in place by an electrode belt 103. The placement of the electrodes 110 is typically transverse to the cranial caudal axis 104 of the patient. Although the electrodes 110 are shown in FIG. 1 as being placed only partially around the patient 105, electrodes 110 may by placed around the entire patient 105 depending on the specific region of interest available or desired for measurement. The electrodes 110 may be coupled to a computing system (not shown) configured to control the operation of the electrodes 110 and perform reconstruction of the EIT image.

Figure 2:
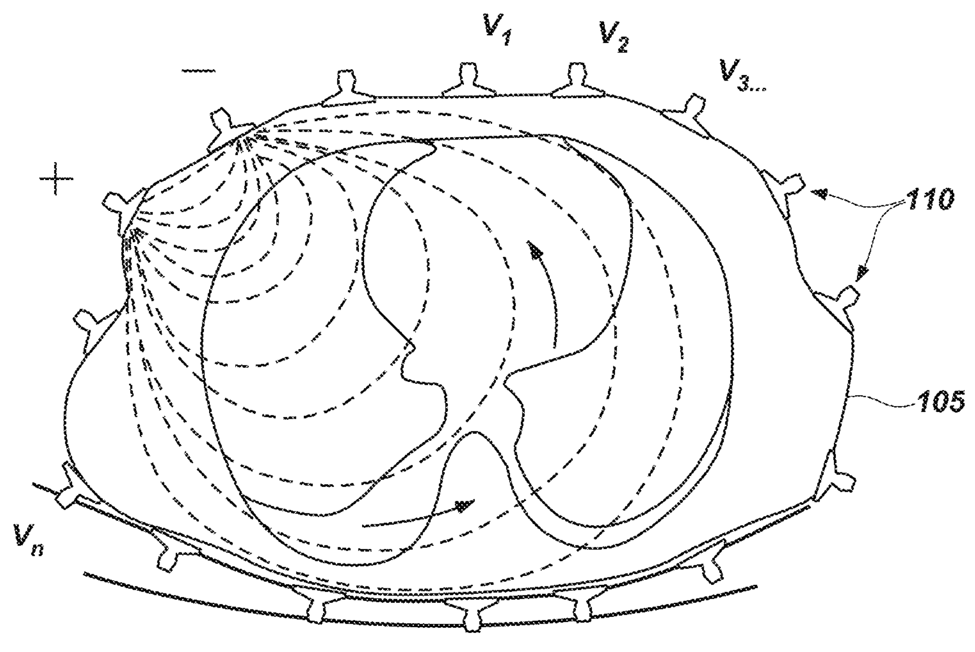
FIG. 2 is a schematic diagram showing a cross-section of the thorax of the patient along the plane of the electrodes according to one or more embodiments of the present disclosure.

FIG. 2 is a schematic diagram showing a cross-section of the thorax of the patient 105 along the plane of the electrodes. A voltage may be applied to a pair of electrodes 110 (shown by the electrodes having a + and − symbol) to inject an excitation current into the patient between an electrode pair. As a result, voltages (e.g., $V_1$, $V_2$, $V_3$ . . . $V_n$) may be detected by the other electrodes and measured by the EIT system 100. Current injection may be performed for a measurement cycle according to a circular pattern using different electrode pairs to generate the excitation current.

Figure 3:
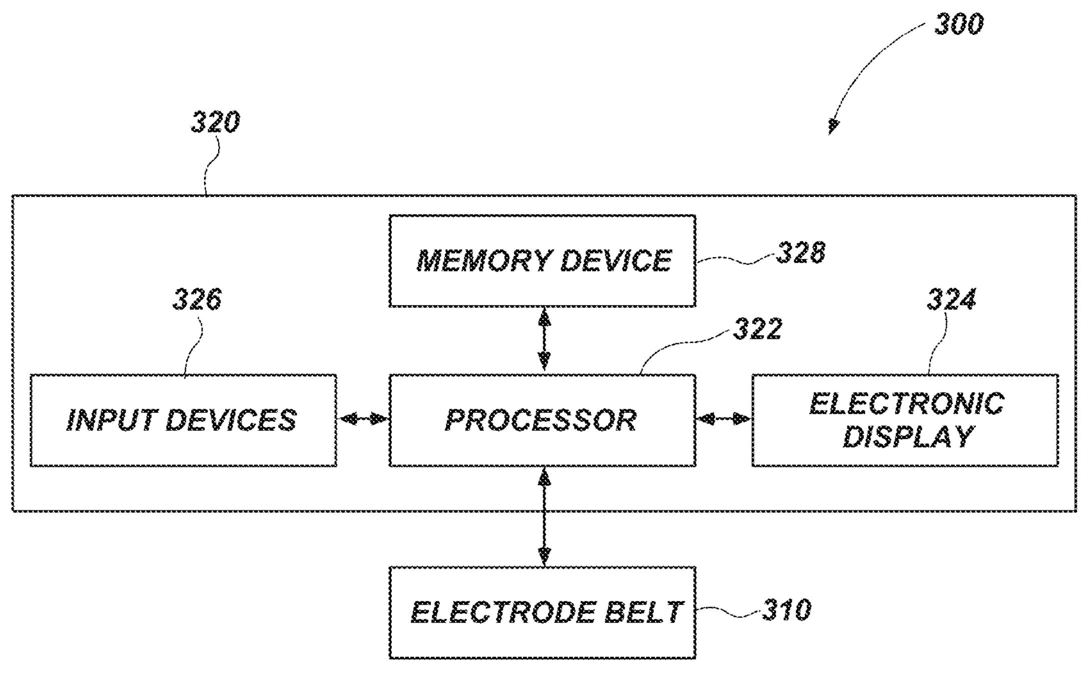
FIG. 3 is a schematic block diagram of an EIT system according to an embodiment of the disclosure.

FIG. 3 is a schematic block diagram of an EIT system 300 according to an embodiment of the disclosure. The EIT system 300 may include an electrode belt 310 operably coupled with a data processing system 320. The electrode belt 310 and the data processing system 320 may be coupled together via a wired connection (e.g., cables) and/or may have communication modules to communicate wirelessly with each other. The data processing system 320 may include a processor 322 operably coupled with an electronic display 324, input devices 326, and a memory device 328. The electronic display 324 may be constructed with the data processing system 320 into a singular form factor for an EIT device coupled with the electrode belt 310. In some embodiments, the electronic display 324 and the data processing system 320 may be separate units of the EIT device coupled with the electrode belt 310. In yet other embodiments, an EIT system 300 may be integrated within another host system configured to perform additional medical measurements and/or procedures, in which the electrode belt 310 may couple to a port of the host system already having its own input devices, memory devices, and electronic display. As such, the host system may have the EIT processing software installed therein. Such software may be built into the host system prior field use or updated after installation.

The processor 322 may coordinate the communication between the various devices as well as execute instructions stored in computer-readable media of the memory device 328 to direct current excitation, data acquisition, data analysis, and/or image reconstruction. As an example, the memory device 328 may include a library of finite element meshes used by the processor 322 to model the patient's body in the region of interest for performing image reconstruction. Input devices 326 may include devices such as a keyboard, touch screen interface, computer mouse, remote control, mobile devices, or other devices that are configured to receive information that may be used by the processor 322 to receive inputs from an operator of the EIT system 300. Thus, for a touch screen interface the electronic display 324 and the input devices 326 receiving user input may be integrated within the same device. The electronic display 324 may be configured to receive the data and output the EIT image reconstructed by the processor for the operator to view. Additional data (e.g., numeric data, graphs, trend information, and other information deemed useful for the operator) may also be generated by the processor 322 from the measured EIT data alone, or in combination with other non-EIT data according to other equipment coupled thereto. Such additional data may be displayed on the electronic display 324.

The EIT system 300 may include components that are not shown in the figures, but may also be included to facilitate communication and/or current excitation with the electrode belt 310 as would be understood by one of ordinary skill in the art, such as including one or more analog to digital converter, signal treatment circuits, demodulation circuits, power sources, etc.

Figure 4:
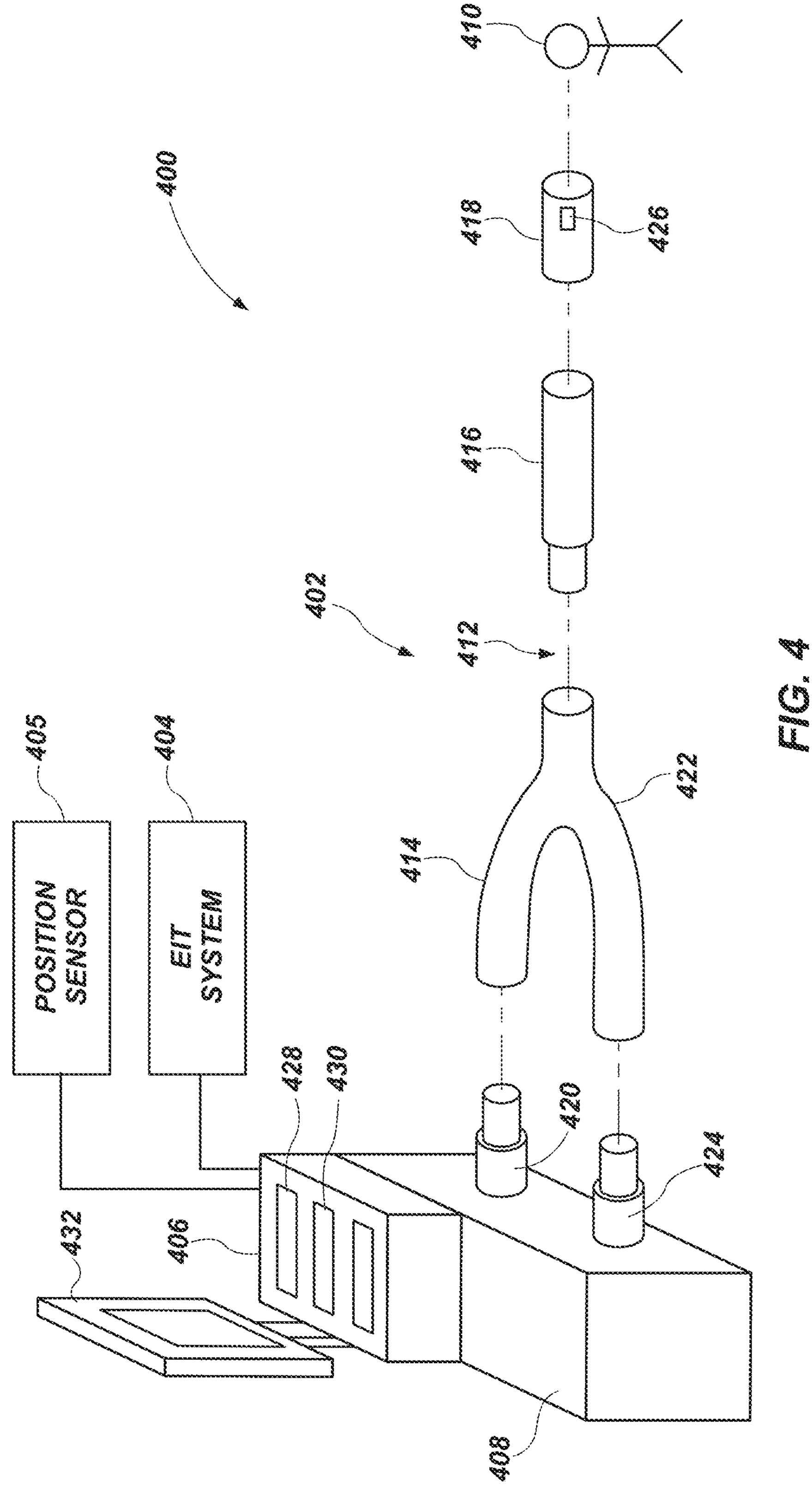
FIG. 4 shows a schematic view of system for identifying a position of a patient, characteristics of lungs of the patient, and a potential recruitment value of a patient's lungs according to one or more embodiments of the present disclosure.

FIG. 4 depicts a schematic view of EIT and position determination system 400 for assessing characteristics of a patient's lungs at differing positions of the patient and at a constant PEEP. For instance, FIG. 4 depicts a system 400 for comparing measurements of a patient's lungs in a first position and in a second position and determining characteristics of the patient's lungs based on the measurements. Referring to FIG. 4, the EIT and position determination system 400 may include a ventilator system 402, an EIT system 404, a position sensor 405, and a controller 406 for operating the system 400 and specifically, the ventilator system 402, the EIT system 404, and the position sensor 405. The ventilator system 402, the EIT system 404, and the position sensor 405 may be operably coupled to the controller 406.

In some embodiments, the ventilator system 402 includes a mechanical ventilator 408 that provides respiratory support or respiratory assistance to a patient 410. For instance, the mechanical ventilator 408 may provide a flow of medical gas, which may include one or more of air, oxygen, nitrogen, and helium. In some embodiments, the flow of medical gas may further include additives such as aerosol drugs or anesthetic agents. The ventilator system 402 may further include a breathing circuit 412, an inspiratory limb 414, a patient limb 416, and a patient connection 418. In some embodiments, the mechanical ventilator 408 may provide a flow of medical gas to the breathing circuit 412 through the inspiratory limb 414, which is connected to an inspiratory port 420 of the mechanical ventilator 408. The medical gas may flow (e.g., travel) through the inspiratory limb 414 and into the patient limb 416 of the breathing circuit 412.

Accordingly, the mechanical ventilator 408 may provide the medical gas to the patient 410 through the patient connection 418.

Expired gases from the patient 410 may be delivered back to the mechanical ventilator 408 through the patient connection 418 and the patient limb 416. In some embodiments, the expired gases may be directed into an expiratory limb 422 of the breathing circuit 412 via one or more valves (e.g., check valves). For instance, the ventilator system 402 may further include a plurality of check valves, which may be placed at various points along the breathing circuit 412 such as to only permit medical gas flow in a desired direction along the appropriate pathway toward or away from the patient 410.

Additionally, the expired gases may be returned to the mechanical ventilator 408 through an expiratory port 424 of the mechanical ventilator 408.

In some embodiments, the expiratory port 424 may include a controllable flow valve that is adjustable to regulate the pressure within the breathing circuit 412. Adjusting the flow valve may create a back pressure, which is applied to the patient 410 during exhalation to create a positive end expiratory pressure ("PEEP"). Accordingly, the system 400 may include any conventional system for providing PEEP therapy to a patient 410. Additionally, other systems and configurations as recognized by one of ordinary skill in the art fall within the scope of the present disclosure.

The ventilator system 402 may further include one or more gas monitoring sensors 426. In some embodiments, the one or more gas monitoring sensors 426 may be disposed within the patient connection 418 of the breathing circuit 412. In alternative embodiments, the one or more gas monitoring sensors 426 may be fluidly connected to any other component of the breathing circuit 412 or the ventilator system 402. In some embodiments, the gas monitoring sensor 426 may include one or more of a pressure, a flow, and a gas concentration sensor. As is described in further detail below, the controller 406 and the mechanical ventilator 408 may utilize the one or more gas monitoring sensors 426 to monitor and ultimately, control the operation of the mechanical ventilator 408 and provide information (e.g., feedback to a user (e.g., clinician)). In some embodiments, the one or more gas monitoring sensors 426 may include any conventional gas sensors. By way of nonlimiting example, the one or more gas monitoring sensors 426 may include one or more of a volumetric sensor, a flow sensor, a pressure sensor, a concentration sensor, or any combination thereof.

The EIT system 404 may include any of the EIT systems described above in regard to FIGS. 1-3 and may operate according to any of the embodiments described above. In some embodiments, the EIT system 404 may include any conventional EIT system. Additionally, as noted above, the EIT system 404 may be operably coupled to the controller 406 and may provide information to controller 406 regarding measurements performed by the EIT system 404. In some embodiments, the EIT system 404 may be completely independent of the ventilator system 402 and may determine PEEP levels via a respective pressure sensor operably coupled to the EIT system 404. In one or more embodiments, the EIT system 404 may also have a respective electronic display and input devices separate from displays and/or input devices of the ventilator system 402. Furthermore, the electronic display and input devices of the EIT system 404 may be utilized to input (e.g., manually input) information about the PEEP and/or other ventilatory parameters.

The position sensor 405 may include a sensor for determining (e.g., identifying) a position and decubitus (e.g., lateral, supine, or prone positions and degrees thereof) of a patient. In some embodiments, the position sensor 405 may include a spatial orientation sensor coupled to a patient and/or to a support of the patient (e.g., the patient's bed or mattress). In additional embodiments, the position sensor 405 may include one or more imagers (e.g., cameras), which may obtain images that are analyzed by the controller 406 to identify a position of the patient. In yet further embodiments, a position of the patient may be determined by analyzing a regional impedance signal and/or regional EIT images. In further embodiments, the position sensor 405 may be operably connected to the patient's support (e.g., the patient's bed) and may determine the position based on information provided by the patient's bed. In yet further embodiments, a position of the patient may be manually input into the EIT and position determination system 400 by a user (e.g., a caregiver of the patient) via a user interface.

The controller 406 may include a processor 428 coupled to a memory 430 and an input/output component 432. The processor 428 may comprise a microprocessor, a field-programmable gate array, and/or other suitable logic devices. The memory 430 may include volatile and/or nonvolatile media (e.g., ROM, RAM, magnetic disk storage media, optical storage media, flash memory devices, and/or other suitable storage media) and/or other types of computer-readable storage media configured to store data. The memory 430 may store algorithms and/or instructions for operating the ventilator system 402 and the EIT system 404, to be executed by the processor 428. For example, the controller 406 may include the data processing system 320 described above in regard to FIG. 3. In some embodiments, the processor 428 is operably coupled to send data to a computing device operatively coupled (e.g., over the Internet) to the controller 406, such as a server or personal computer. The input/output component 432 can include a display, a touch screen, a keyboard, a mouse, and/or other suitable types of input/output devices configured to accept input from and provide output to an operator.

Referring still to FIG. 4, as is described in greater detail below in regard to FIGS. 5-9, the system 400 may utilize the ventilator system 402 to apply a constant PEEP level to a patient while the patient's position is changed. Changing the patient's position may increase a base line pressure within at least a portion of the patient's respiratory system. Conventional PEEP pressures range up to 40 $cmH_2O$, although higher PEEP pressures may also be used. High PEEP refers to PEEP therapy applied above 10 $cmH_2O$, and more specifically, 10-30 $cmH_2O$. Low PEEP refers to PEEP pressures below 10 $cmH_2O$, and which are often applied at 5-8 $cmH_2O$.

In some embodiments, the effects of applying PEEP to a patient are measured by measuring a volume of the patient's lungs in response to the application of PEEP. After PEEP application, the volume of the patient's lungs is measured as the end expiratory lung volume (EELV) and is measured for a particular PEEP pressure applied to the patient. In some embodiments, EELV is measured at zero PEEP ("ZEEP"). The measurement of EELV at ZEEP is referred to herein as functional residual capacity ($FRC_{ZEEP}$) and is a measurement of the volume of air that remains in the lungs at the end of natural expiration. In some embodiments, when utilizing the EIT system 404 to measure and/or determine EELV, the $FRC_{ZEEP}$ can, in some instances, be considered to be zero such that the FRC does not affect certain calculations. In view of the foregoing, EELV is $FRC_{ZEEP}$ plus lung volume increased by the applied PEEP.

Increases in EELV associated with the application of PEEP come from two physiological sources. A first physiological source of volume increase results from the application of additional pressure on the lung tissue. Applying additional pressure on lung tissue causes the lungs and already-opened alveoli to distend (e.g., swell due to pressure inside the lungs), creating more lung volume. Distending the lungs presents risks to a patient in the form of volutrauma (i.e., local over distention of normal alveoli), which damages the lungs. Volutrauma can result in medical complications with the patient similar to Acute Respiratory Distress Syndrome (ARDS). A second physiological source of increased lung volume is the "recruitment" of alveoli in a process known as "pop-open," where an internal volume of one alveolus suddenly jumps from a zero volume (e.g., collapsed) to a volume attained by neighboring alveoli (e.g., neighboring units). As is known in the art, alveoli are the air sacs within the lungs that promote gas exchange with a patient's blood. Some alveoli, particularly diseased or distressed alveoli, collapse when the pressure within the lungs falls too low, with the alveoli (e.g., unit) attaining or reaching a zero volume. Applying PEEP to a patient (e.g., applying a PEEP therapy) can maintain a minimum airway pressure within the lungs and, in some instances, cause alveoli (e.g., collapsed alveoli) to remain open.

The alveoli can only generate some gas exchange when the alveoli are open. Therefore, in order to maintain some gas exchange when PEEP is insufficient, there is a need of higher driving inspiratory pressure to hyperventilate the already opened alveoli in order to compensate for the lack of function of the closed alveoli (e.g., units). Increased respiratory force causes greater distension on the remaining open alveoli, which may result in further damage to the lung tissue. In contrast, when PEEP is sufficient, the gas exchange is shared among most alveoli (e.g., units), which decreases the driving inspiratory pressure and, in some instances, lung damage. The recruitment of alveoli, therefore, also increases EELV, which correspond to the extra-volume generated by the pop-open of multiple alveolar units. The extra-volume created by opened alveolar units is known as the volume-gain (or vertical displacement in a pressure-volume plot) of the lung at a certain pressure. In a graph having two pressure-volume plots representing lung inflation with a first plot representing the inflation of the lung in a case of no recruitment, and with a second plot representing the conditional inflation of the lung when lung alveoli (e.g., units) were opened since a beginning of inflation, a vertical distance between the two curves represents a volume-gain caused by recruitment.

Figure 5:
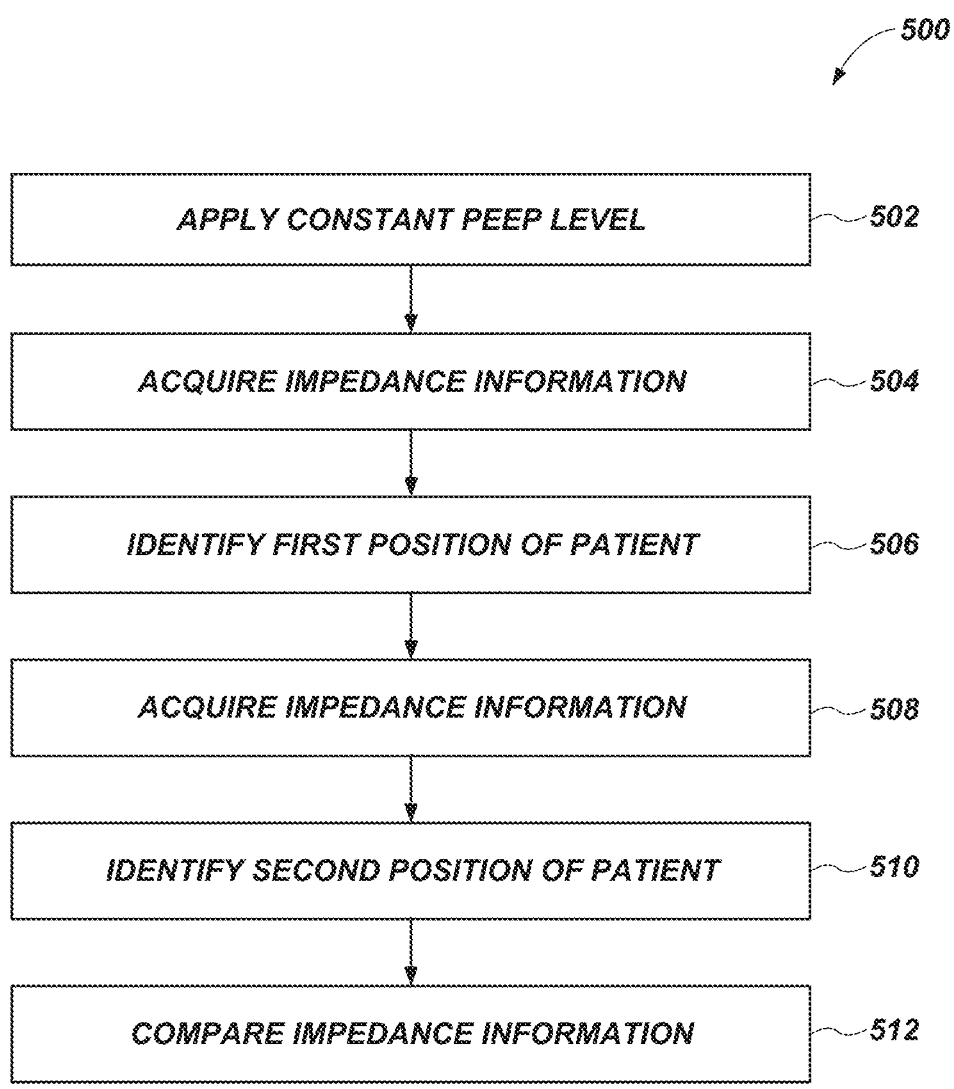
FIG. 5 is a flow chart of a method of determining characteristics of a patient's lungs according to one or more embodiments of the present disclosure.

FIG. 5 shows a method through which the EIT and position determination system 400 may assess characteristics regarding a patient's lungs, perfusion, and/or ventilation.

In some embodiments, the method 500 may include applying a constant PEEP level to lungs of a patient, as shown in act 502. As used herein, the term "constant PEEP" may refer to an at least substantially constant PEEP level (e.g., within plus or minus 2cm$H_2O$). In one or more embodiments, the PEEP level may be between about 10 cm$H_2O$ and about 30 cm$H_2O$. The PEEP may be applied via conventional manners and via any of the systems described herein.

Additionally, the method 500 may include acquiring impedance information regarding the lungs of the patient and determining a first position of the patient, as shown in acts 504 and 506 of FIG. 5. In some embodiments, act 504 may include measuring an end expiratory lung impedance ("EELZ") of the lungs of the patient while the patient is in a first position (e.g., a supine position). In some embodiments, measuring an EELZ of the lungs of the patient at the applied PEEP may include determining an impedance value represented in EIT images of the lungs of the patient. Furthermore, the EELZ may be representative of an end expiratory lung ("EELV"). For instance, the EELV of the lungs may be determined based on (e.g., from) the measured EELZ of the lungs. As will be appreciated in view of the present disclosure, in some embodiments, act 504 may include determining an EELZ of just a region (e.g., at least one region, a region of interest, etc.) of a lung of the patient. In some embodiments, act 504 may further include directly determining and/or measuring an EELV of the lungs of the patient at the applied PEEP via the one or more gas monitoring sensors 426 described above in regard to FIG. 4. For instance, the one or more gas monitoring sensors 426 may include one or more of a volumetric sensor, a flow sensor, a pressure sensor, a concentration sensor, or any combination thereof. Furthermore, the EELV may be measured and/or determined via a variety of methods including body plethysmography, helium dilution, inert gas-wash out techniques, or any other conventional method known in the art.

Additionally, act 504 of the method 500 may further include determining a chord-compliance (or pressure-volume relationship) of the lungs (e.g., at least one region of a lung) of the patient at the applied PEEP. In some embodiments, act 504 may include obtaining an EIT image of at least a portion of the lungs of the patient at the applied PEEP. For example, act 504 may include generating (e.g., reconstructing) EIT images via any of the manners described above in regard to FIGS. 1-4 and utilizing any of the EIT systems described above in regard to FIGS. 1-4.

In some embodiments, act 504 may include determining a chord-compliance of the lungs of the patient on a pixel by pixel level. For instance, act 504 may include determining a chord-compliance indicated by each pixel of each generated EIT image based at least partially on the impedance indicated by each pixel of each generated EIT image.

Furthermore, an EIT plethysmograph includes a waveform that is derived from a sum of pixels within a given region of interest of an EIT image (or the entire EIT image) (frame) plotted against time. In particular, the EIT plethysmograph represents an amount of air that moves in and out of the region of interest (referred to herein as tidal oscillation ($\Delta Z_{VT}$)). The tidal oscillation in the EIT plethysmograph correlates to a change in lung volume estimated by computerized tomography. Additionally, changes in EELVs correlate to the change in end-expiratory lung impedance (EELZ) demonstrated in the generated EIT images. Thus, the generated EIT images indicate changes in pulmonary aeration (via ΔEELZ) caused by, for example, position changes, as described herein.

In view of the foregoing, the EIT images are a representation of the tidal changes in impedance pixel by pixel. In other words, the EIT images represent a color map of the pixel wise ΔZ (e.g., $\Delta Z_{VT}$). Accordingly, based on the EIT images, a distribution of ventilation in given direction (e.g., ventral-to-dorsal direction) for the applied PEEP can be determined. Furthermore, based on the pixel wise ΔZ, at the applied PEEP, a compliance can be calculated from an amount of air entering the lungs (ΔZ) and the difference between a plateau pressure ($P_{plateau}$) and the applied PEEP (e.g., an elastic pressure of the lungs). For instance, because the plateau pressure ($P_{plateau}$) and the applied PEEP can be substituted for inspiratory and expiratory alveolar pressures at zero flow, a compliance of each EIT image pixel can be estimated as:

$$Compliance_{pixel} = \frac{\Delta Z}{P_{plateau} - \text{PEEP}} \quad (1)$$

Based on the determined compliance of each pixel, a sum of the determined compliances of each pixel of a given EIT image yields an overall compliance of the image (e.g., an overall compliance of the lungs of the patients at a given PEEP). Likewise, a sum of the determined compliances of each pixel within a region of interest of an EIT image yields an overall compliance of the region of interest.

Referring again to FIG. 5, in one or more embodiments, act 506 may include identifying a first position of the patient (FIGS. 6A and 6B). For example, as depicted in FIGS. 6A and 6B, the first position may include a position where the patient's spinal cord extends generally perpendicular to a gravity vector, and the patient's torso and face may face upward. For instance, the first position may be a general supine position (i.e., a position where the patient faces upward). In additional embodiments, the first position may be a first lateral decubitus position where the patient is tilted to one side with the spinal cord remaining generally perpendicular to the gravity vector. Furthermore, while particular positions are depicted herein, the first position may include any lateral decubitus, supine, prone, and/or intermediate position.

As depicted in FIG. 6B, a second position may include a second lateral decubitus position where the patient is tilted to one side with the spinal cord remaining generally perpendicular to the gravity vector. For instance, the second position may include a lateral position. Furthermore, while particular positions are depicted herein, the second position may include any lateral decubitus, supine, prone, and/or intermediate position. Referring still to FIGS. 5, 6A, and 6B together, in some embodiments, act 506 may include determining the first position of the patient via a spatial orientation sensor coupled (e.g., attached) to the patient and/or a patient's support (e.g., the patient's bed). The spatial orientation sensor may include one or more of a magnetometer, an accelerometer, a gyroscope, an inertial measurement device, and/or any other known spatial orientation sensor. In additional embodiments, act 506 may include determining the first position of the patient via analyzing images obtained through an imager system. For instance, act 506 may include using image recognition methods to identify a patient's position and/or change in position by analyzing, via know methods, images of the patient's position. In further embodiments, act 506 may include exchanging information with a patient's support to determine the orientation of the patient. For example, act 506 may include exchanging information with the patient's support (e.g., bed) to determine an orientation of the support, and as a result, an orientation of the patient. In yet further embodiments, act 506 may include identifying a position of the patient by analyzing regional impedance signals or regional EIT images obtained in act 504. In yet further embodiments, act 506 may include receiving an indication of a position of the patient via a user interface of the EIT and position determination system 400. Identifying a position of the patient by analyzing regional impedance signal or regional EIT images is described in greater detail below in regard to FIG. 8.

Additionally, the method 500 may include acquiring impedance information regarding the lungs of the patient and identifying a second position of the patient, as shown in acts 508 and 510 of FIG. 5. For example, the patient may be moved from the first position to the second position, and subsequently, the EIT and position determination system 400 may acquire impedance information that is characterized by the second position and may identify the second position. The PEEP may remain at least substantially constant during the first position and the second position of the patient. The impedance information (e.g., second impedance information) and the second position of the patient may be determined via any of the manners described above in regard to acts 504 and 506 of FIG. 5. Furthermore, the second position of the patient may include any of the positions described above in regard to FIGS. 6A and 6B. Moreover, while the first and second positions are described herein as being identified by the EIT and position determination system 400, the disclosure is not so limited. For instance, in some embodiments, data regarding the first and second positions may be input into the EIT and position determination system 400 by a user (e.g., an administrator).

Upon acquiring impedance information regarding the lungs of the patient and determining a second position of the patient, the method may include comparing the impedance information of the first position with the impedance information of the second position, as shown in act 512 of FIG. 5. In some embodiments, act 512 may include determining one or more of a change in compliance, a change in regional Tidal Volume (i.e., Tidal Impedance), and/or a change in aeration (e.g., a change in end expiratory lung volume, a change in end expiratory lung impedance, a change in a baseline of a plethysmograph, etc.). For example, act 512 may include determining characteristics and/or changes in characteristics (e.g., measurements) via any of the manners described in U.S. application Ser. No. 16/272,600, to Holzhacker, filed Feb. 11, 2019, and titled: "Systems and methods to determining a patient's responsiveness to an alveolar recruitment maneuver," the disclosure of which is incorporated in its entirety by reference herein.

Furthermore, based on the comparison described above in regard to act 512, the EIT and position determination system 400 may determine a potential lung recruitment value for a patient, an effective PEEP value, etc. Furthermore, based on the comparison, the EIT and position determination system 400 may determine any of the values (e.g., a potential lung recruitment value), characteristics, and indexes described in U.S. application Ser. No. 16/272,600, to Holzhacker, filed Feb. 11, 2019, and titled: "Systems and methods to determining a patient's responsiveness to an alveolar recruitment maneuver," the disclosure of which is incorporated in its entirety by reference herein.

In some embodiments, the comparison may be for a region of the lungs of the patient in the first position and the second position. Furthermore, in some embodiments, when the patient is in the first position, the region may be above a horizontal plane (602 in FIGS. 6A and 6B) within which a horizontal axis piercing a centroid of the spinal cord generally lies, and when the patient is in the second position, the region may be below the horizontal plane. Alternatively, in some embodiments, in some embodiments, when the patient is in the first position, the region may be below the horizontal plane, and when the patient is in the second position, the region may be above the horizontal plane.

FIG. 7A shows a graph that depicts impedance information from a patient in a left lateral decubitus position (CUR) compared with the patient in a supine position (REF) (i.e., action 1). Furthermore, the graph shows a higher aeration level and lower Tidal Volume ($V_t$) in the right lung. Moreover, the graph also shows an improved regional compliance in the left lung and impaired compliance in the right lung.

FIG. 7B shows the graph depicting values for a returned supine position (CUR) compared with the patient in the original supine position (REF) (i.e., action 2). Furthermore, the graph shows a higher aeration level in the left lung and globally. Moreover, the graph shows that compliance of the left lung was improved. The foregoing indicates that the applied PEEP level (the constant PEEP level) was sufficient to sustain recruitment of alveoli that occurred during the left lateral decubitus positions described above in regard to FIG. 7A.

FIG. 7C shows the graph depicting values for the patient in a right lateral decubitus position (CUR) compared with the patient in a supine position (REF) (i.e., action 3). Furthermore, the graph shows a higher aeration level and lower $V_t$ in the left lung. Moreover, the graph also shows an improved regional compliance in the right lung and impaired compliance in the left lung.

FIG. 7D shows the graph depicting values for a second returned supine position (CUR) compared with the patient in the original supine position (REF) (i.e., action 4). Furthermore, the graph shows a higher aeration level in the left lung, the right lung, and globally. Moreover, the graph shows that compliance of the left lung and the right lung were improved. The foregoing indicates that the applied PEEP level (the constant PEEP level) was sufficient to sustain recruitment of alveoli that occurred during the left and right lateral decubitus positions described above in regard to FIG. 7A.

FIG. 8 shows a graph depicting a global EIT plethysmograph and a regional EIT plethysmograph (i.e., left and right EIT plethysmographs) measured and obtained while orienting the patient in the positions described in regard to actions 1-4 referred to in regard to FIGS. 7A-7B.

As mentioned above, the EIT and position determination system 400 may utilize right and/or left EIT plethysmographs to assess a patient's lateral positioning as well as changes in the patient's lateral decubitus. For instance, during a "LEFT DOWN" phase (e.g., a left lateral position), the right and left EIT plethysmographs show a significant increase in the baseline of the right plethysmogram as well as a decrease of the baseline of the left plethysmograph. Furthermore, the right and left EIT plethysmographs show that a baseline of the right plethysmogram was still increasing when the patient was moved back to a supine position. The foregoing indicates that the patient was still recruiting and could further benefit more from the LEFT DOWN position.

Additional, during a "RIGHT DOWN" phase (e.g., a right lateral position), the right and left EIT plethysmographs show a significant increase in the baseline of the left plethysmogram as well as a decrease of the baseline of the right plethysmograph. Furthermore, the right and left EIT plethysmographs show that a baseline of the left plethysmogram was still increasing when the patient was moved back to a supine position. The foregoing indicates that the patient was still recruiting and could further benefit more from the RIGHT DOWN position.

In the example depicted in FIG. 8, a PEEP level of 17 $cmH_2O$ was applied to the patient, and the patient exhibited a sustained and significant increase in a baseline of the plethysmograph (e.g., aeration or FRC shown within the global plethysmograph of FIG. 8). The foregoing indicates that the PEEP level is sufficient to effectuate recruitment for the patient. Furthermore, the PEEP level was assessed without any need of increasing or changing a PEEP level.

Figure 9:
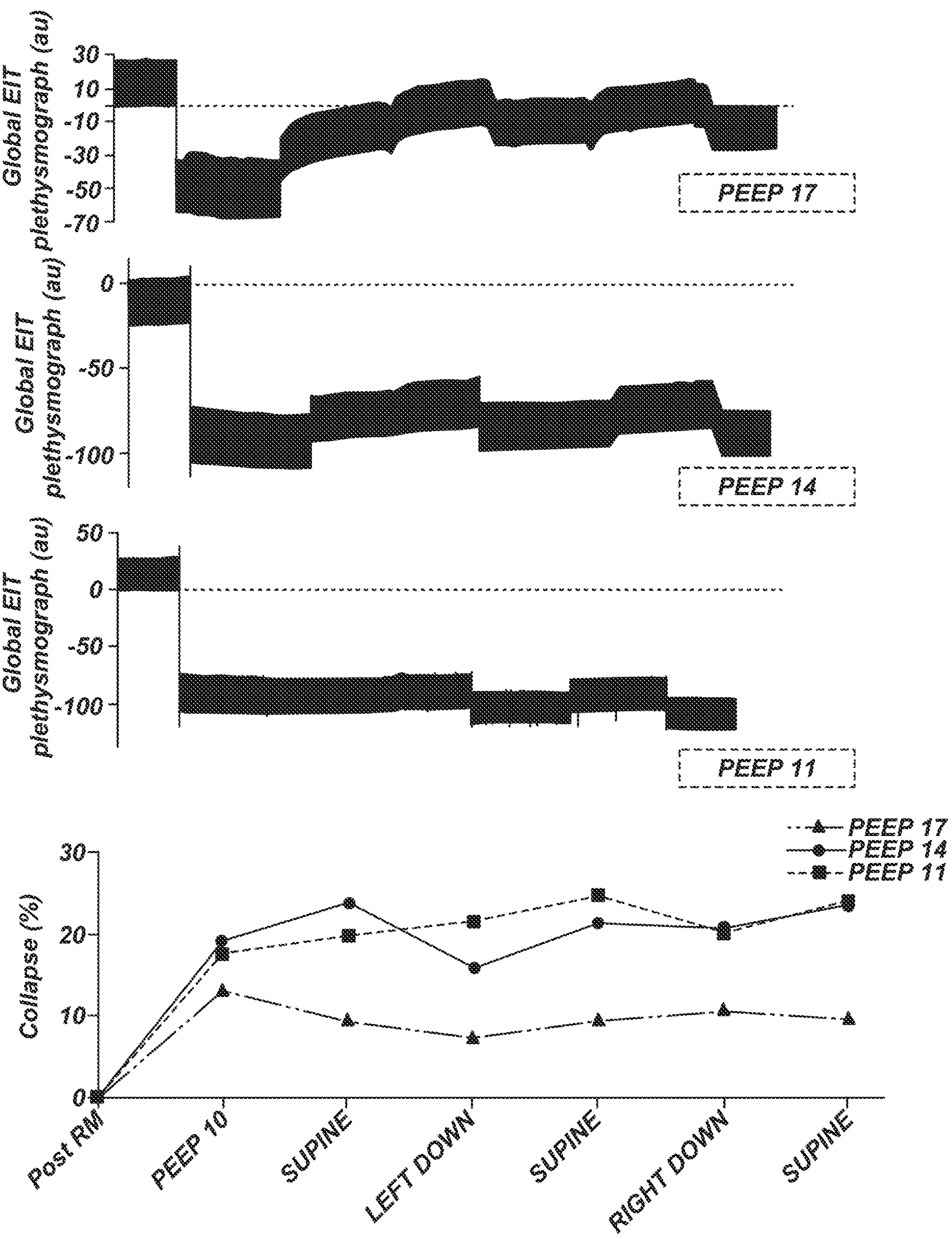
FIG. 9 shows a graph depicting global EIT plethysmograph of a patient at varying PEEP levels.

FIG. 9 shows a graph depicting global EIT plethysmograph of a patient at varying PEEP levels. As shown in FIG. 9, lateral positioning of the patient (e.g., subjecting the patient to the RIGHT DOWN and LEFT DOWN positions described above) with PEEP levels of 11 $cmH_2O$ and 14 $cmH_2O$ did not result in a sustained and significate increase in the baseline of the plethysmograph or an improvement of a regional compliance. The foregoing indicates that the PEEP levels of 11 $cmH_2O$ and 14 $cmH_2O$ were not sufficient to recruit and maintain recruitment of alveoli (e.g., maintain the alveoli open).

Referring to FIGS. 1-9 together, the EIT and position determination system 400 and methods described herein provide advantages over conventional methods. For instance, the EIT and position determination system 400 enables regional assessment of lung function and responsiveness to ventilator maneuvers at the bedside without radiation and without increasing and/or changing PEEP. Furthermore, the EIT and position determination system 400 enables regional assessment of lung function in patients that are not intubated.

The EIT and position determination system 400 and methods described herein further provide guide maneuvers (e.g., changing the position of the patient from supine to a left lateral position) that identify a best position and optimize ventilator settings (e.g., a PEEP level) to maximize responsiveness to ventilator maneuvers while applying a lowest possible PEEP level as to not damage the lungs of the patient and/or impair hemodynamics of the lungs and while keeping alveoli open.

Moreover, the EIT and position determination system 400 and methods described herein enable assessment of the effect of a lateral positioning maneuver, e.g., a recruitment of previously collapsed areas or further impairment of the homogeneity of ventilation.

Embodiments of the present disclosure further include the following embodiments.

Embodiment 1. A method for assessing a characteristic of a lung of a patient, the method comprising: during an applied positive end expiratory pressure between 0 and 40 $cmH_2O$, identifying a first position of a patient; acquiring first impedance data representative of at least one region of the patient's lung when the patient is in the first position; during the applied positive end expiratory pressure, identifying a second different position of the patient; acquiring second impedance data representative of at least the region of the patient's lung when the patient is in the second position; comparing the first impedance data with the second impedance data; and determining whether the applied positive end expiratory pressure is sufficient to effectuate or sustain alveoli recruitment.

Embodiment 2. The method of claim 1, wherein acquiring first impedance data comprises measuring a first end expiratory lung impedance in the at least one region of the lung while the patient is in the first position.

Embodiment 3. The method of claim 2, wherein acquiring second impedance data comprises measuring a second end expiratory lung impedance in the at least one region of the lung while the patient is in the second position.

Embodiment 4. The method of any one of embodiments 1-3, wherein acquiring first impedance data comprises acquiring impedance data related to a region of the lung that is located above a horizontal plane within which a horizontal axis piercing a centroid of the spinal cord lies when the patient is in the first position, and wherein acquiring second impedance data comprises acquiring impedance data related to the region of the lung that is located below the horizontal plane when the patient is in the second position.

Embodiment 5. The method of any one of embodiments 1-4, wherein comparing the first impedance data with the second impedance data comprises determining a change in end expiratory lung impedance in the at least one region of the lung.

Embodiment 6. The method of any one of embodiments 1-5, wherein comparing the first impedance data with the second impedance data comprises determining a change in regional tidal volume.

Embodiment 7. The method of any one of embodiments 1-6, wherein comparing the first impedance data with the second impedance data comprises determining a change in end expiratory lung volume in the at least one region of the lung.

Embodiment 8. The method of any one of embodiments 1-7, wherein the first position comprises a supine position, and wherein the second position comprises a lateral position.

Embodiment 9. The method of any one of embodiments 1-8, further comprising: during the applied positive end expiratory pressure, determining that the patient has returned to the first position; acquiring third impedance data representative of the at least one region of patient's lung when the patient is in the returned first position; and comparing the first impedance data with the third impedance data.

Embodiment 10. The method of any one of embodiments 1-9, further comprising: during the applied positive end expiratory pressure, identifying a third different position of the patient; acquiring fourth impedance data representative of the at least one region of patient's lung when the patient is in the third position; and comparing the first impedance data with the fourth impedance data.

Embodiment 11. A system for assessing a characteristic of a lung of a patient, the system comprising: at least one processor; and at least one non-transitory computer readable storage medium storing instructions thereon that, when executed by the at least one processor, cause the at least one processor to: identify a first position of the patient; acquire first impedance data of the patient's lung, the first impedance data reflecting the first position of the patient; identify a second different position of the patient; acquire second impedance data of the patient's lung, the second impedance data reflecting the second position of the patient; and compare the first impedance data with the second impedance data to identifying a change in a characteristic of the patient's lung.

Embodiment 12. The system of embodiment 11, wherein identifying a first position of the patient comprises identifying the first position of the patient via a spatial orientation sensor attached to the patient.

Embodiment 13. The system of any one of embodiments 11 and 12, wherein identifying a first position of the patient comprises: capturing images of the patient; analyzing the images of the patient to identify the first position of the patient.

Embodiment 14. The system of any one of embodiments 11-13, wherein identifying a first position of the patient comprises: receiving data from a patient support regarding an orientation of the patient support; and determining the first position of the patient based on data received from the patient support.

Embodiment 15. The system of any one of embodiments 11-14, wherein identifying a first position of the patient comprises acquiring the first impedance data of the patient's lung and determining the first position of the patient based on the first impedance data.

Embodiment 16. The system of any one of embodiments 11-15, further comprising instructions that, when executed by the at least one processor, cause the at least one processor to determine whether the applied positive end expiratory pressure is sufficient to effectuate or sustain recruitment.

Embodiment 17. The system of any one of embodiments 11-16, wherein comparing the first impedance data with the second impedance data comprises determining a change in compliance in at least one region of the lung.

Embodiment 18. The system of embodiment 17, wherein determining a change in compliance comprises: determining a compliance represented by each pixel of a first electrical impedance tomography image within the first impedance data; and determining a compliance represented by each pixel of a second electrical impedance tomography image within the second impedance data.

Embodiment 19. A system for determining a potential lung recruitment value for a patient, the system comprising: a ventilator system; an electrical impedance tomography system; a position sensor; and a controller, wherein the ventilator system, the electrical impedance tomography system, and the position sensor are operably coupled to the controller, the controller comprising: at least one processor; and at least one non-transitory computer readable storage medium storing instructions thereon that, when executed by the at least one processor, cause the at least one processor to: cause the ventilator system to apply and maintain a positive end expiratory pressure to a patient; identify a first position of the patient; acquire first impedance data of the patient's lung, the first impedance data reflecting the first position of the patient; identify a second different position of the patient; acquire second impedance data of the patient's lung, the second impedance data reflecting the second position of the patient; compare the first impedance data with the second impedance data to identifying a change in a characteristic of the patient's lung; and determine whether the applied positive end expiratory pressure is sufficient to effectuate or sustain recruitment.

Embodiment 20. The system of embodiment 19, wherein the first position comprises a supine position, and wherein the second position comprises a lateral position.

Embodiment 21. The system of any one of embodiments 19 and 20, further comprising instructions that, when executed by the at least one processor, cause the controller to communicate with a patient support and transmit control signals to control the patient's position based at least partially on the characteristic of the patient's lung.

While the present disclosure has been described herein with respect to certain illustrated embodiments, those of ordinary skill in the art will recognize and appreciate that it is not so limited. Rather, many additions, deletions, and modifications to the illustrated embodiments may be made without departing from the scope of the disclosure as hereinafter claimed, including legal equivalents thereof. In addition, features from one embodiment may be combined with features of another embodiment while still being encompassed within the scope of the disclosure. Further, embodiments of the disclosure have utility with different and various detector types and configurations.

What is claimed is:

1. A method for assessing a characteristic of a lung of a patient, the method comprising:

applying and maintaining a constant positive end expiratory pressure between 0 and 40cm$H_2O$ to the patient with a ventilator system;

during the constant positive end expiratory pressure, identifying a first position of the patient;

during the constant positive end expiratory pressure, acquiring first impedance data representative of at least one region of the patient's lung comprising a portion of the lung less than the entire lung when the patient is in the first position;

during the constant positive end expiratory pressure, identifying a second different position of the patient;

during the constant positive end expiratory pressure, acquiring second impedance data representative of the at least one region of the patient's lung when the patient is in the second position;

comparing the first impedance data with the second impedance data to identify a change in a characteristic of the patient's lung;

determining that the patient has returned to the first position;

acquiring third impedance data of the at least one region of the patient's lung, the third impedance data reflecting the first position of the patient; and comparing the first impedance data with the third impedance data to determine whether the applied constant positive end expiratory pressure is sufficient to effectuate or sustain recruitment.

2. The method of claim 1, wherein acquiring the first impedance data comprises measuring a first end expiratory lung impedance in the at least one region of the lung while the patient is in the first position.

3. The method of claim 2, wherein acquiring the second impedance data comprises measuring a second end expiratory lung impedance in the at least one region of the lung while the patient is in the second position.

4. The method of claim 1, wherein acquiring the first impedance data comprises acquiring impedance data related to a region of the lung that is located above a horizontal plane within which a horizontal axis piercing a centroid of the spinal cord lies when the patient is in the first position, and wherein acquiring the second impedance data comprises acquiring impedance data related to the region of the lung that is located below the horizontal plane when the patient is in the second position.

5. The method of claim 1, wherein comparing the first impedance data with the second impedance data comprises determining a change in end expiratory lung impedance in the at least one region of the lung.

6. The method of claim 1, wherein comparing the first impedance data with the second impedance data comprises determining a change in regional tidal volume.

7. The method of claim 1, wherein comparing the first impedance data with the second impedance data comprises determining a change in end expiratory lung volume in the at least one region of the lung.

8. The method of claim 1, wherein the first position comprises a supine position, and wherein the second position comprises a lateral position.

9. The method of claim 1, further comprising:

during the constant positive end expiratory pressure, identifying a third different position of the patient;

acquiring fourth impedance data representative of the at least one region of the patient's lung when the patient is in the third position; and comparing the first impedance data with the fourth impedance data.

10. A system for assessing a characteristic of a lung of a patient, the system comprising:

a ventilator system;

at least one processor; and at least one non-transitory computer readable storage medium storing instructions thereon that, when executed by the at least one processor, cause the at least one processor to:

cause the ventilator system to apply and maintain a constant positive end expiratory pressure to the patient and, while maintaining the constant positive end expiratory pressure:

identify a first position of the patient;

acquire first impedance data of a first region of interest of the patient's lung comprising a portion of the lung less than the entire lung, the first impedance data reflecting the first position of the patient;

identify a second different position of the patient;

acquire second impedance data of the first region of interest of the patient's lung, the second impedance data reflecting the second position of the patient;

compare the first impedance data with the second impedance data to identify a change in a characteristic of the patient's lung;

determine that the patient has returned to the first position;

acquire third impedance data of the first region of interest of the patient's lung, the third impedance data reflecting the first position of the patient; and compare the first impedance data with the third impedance data to determine whether the applied constant positive end expiratory pressure is sufficient to effectuate or sustain recruitment.

11. The system of claim 10, wherein identifying the first position of the patient comprises identifying the first position of the patient via a spatial orientation sensor attached to the patient.

12. The system of claim 10, wherein identifying the first position of the patient comprises:

capturing images of the patient; and analyzing the images of the patient to identify the first position of the patient.

13. The system of claim 10, wherein identifying the first position of the patient comprises:

receiving data from a patient support regarding an orientation of the patient support; and determining the first position of the patient based on the data received from the patient support.

14. The system of claim 10, wherein identifying the first position of the patient comprises acquiring the first impedance data of the first region of interest of the patient's lung and determining the first position of the patient based on the first impedance data.

15. The system of claim 10, wherein comparing the first impedance data with the second impedance data comprises determining a change in compliance in the first region of interest of the patient's lung.

16. The system of claim 15, wherein determining the change in compliance comprises:

determining a compliance represented by each pixel of a first electrical impedance tomography image within the first impedance data; and determining a second compliance represented by each pixel of a second electrical impedance tomography image within the second impedance data.

17. A system for determining a potential lung recruitment value for a patient, the system comprising:

a ventilator system;

an electrical impedance tomography system;

a position sensor; and a controller, wherein the ventilator system, the electrical impedance tomography system, and the position sensor are operably coupled to the controller, the controller comprising:

at least one processor; and at least one non-transitory computer readable storage medium storing instructions thereon that, when executed by the at least one processor, cause the at least one processor to:

cause the ventilator system to apply and maintain a constant positive end expiratory pressure to the patient; and, while maintaining the constant positive end expiratory pressure:

identify a first position of the patient;

acquire first impedance data of a first region of interest of the patient's lung comprising a portion of the lung less than the entire lung, the first impedance data reflecting the first position of the patient;

identify a second different position of the patient;

acquire second impedance data of the first region of interest of the patient's lung, the second impedance data reflecting the second position of the patient;

compare the first impedance data with the second impedance data to identify a change in a characteristic of the patient's lung;

determine that the patient has returned to the first position;

acquire third impedance data of the first region of interest of the patient's lung, the third impedance data reflecting the first position of the patient; and compare the first impedance data with the third impedance data to determine whether the applied constant positive end expiratory pressure is sufficient to effectuate or sustain recruitment.

18. The system of claim 17, wherein the first position comprises a supine position, and wherein the second position comprises a lateral position.

19. The system of claim 17, further comprising instructions that, when executed by the at least one processor, cause the controller to communicate with a patient support and transmit control signals to control the patient's position based at least partially on the characteristic of the patient's lung.

* * * * *